United States Patent [19]
Greindl et al.

[11] Patent Number: 6,093,848
[45] Date of Patent: Jul. 25, 2000

[54] PREPARATION OF SUBSTITUTED GUANIDINE DERIVATIVES

[75] Inventors: Thomas Greindl, Bad Dürkheim; Günter Scherr, Ludwigshafen; Rolf Schneider, Mannheim; Klaus Mundinger, Limburgerhof, all of Germany

[73] Assignee: BASF Aktiengesellschaft, Ludwigshafen, Germany

[21] Appl. No.: 09/179,093

[22] Filed: Oct. 27, 1998

[30] Foreign Application Priority Data

Nov. 4, 1997 [DE] Germany ............... 197 48 696

[51] Int. Cl.⁷ ............... C07C 249/02; C07C 251/02
[52] U.S. Cl. ............... 562/560; 564/231; 564/241
[58] Field of Search ............... 564/230, 231, 564/241; 562/560

[56] References Cited

U.S. PATENT DOCUMENTS

| | | | |
|---|---|---|---|
| 2,820,822 | 1/1958 | Skelly ............... | 260/534 |
| 4,421,602 | 12/1983 | Brunnmueller et al. ............... | 162/168 |
| 4,680,300 | 7/1987 | Nelson et al. ............... | 514/312 |
| 4,774,285 | 9/1988 | Pfohl et al. ............... | 525/60 |
| 4,900,740 | 2/1990 | Muller et al. ............... | 514/381 |
| 4,978,427 | 12/1990 | Pfohl et al. ............... | 162/168 |
| 5,719,319 | 2/1998 | Weiss et al. ............... | 562/560 |
| 5,739,328 | 4/1998 | Schafer et al. ............... | 544/194 |
| 5,969,182 | 10/1999 | Greindl et al. ............... | 562/560 |

FOREIGN PATENT DOCUMENTS

| | | |
|---|---|---|
| 55004349 | 6/1978 | Japan. |
| 7877365 | 6/1978 | Japan. |
| 55-004350 | 1/1980 | Japan. |
| 817749 | 8/1959 | United Kingdom. |

OTHER PUBLICATIONS

J. Am. Chem. Soc., 76, 1954, 4283–85.
Chem. Ztg., 98 (12), 1974, 617–618.
Z. Phys. Chem., 279 (1943), 52–59.
J. Pppl. Chem 4 (1954) 283–292.
Chem. Ber., (1900), 1517–1519.
Rec. Trav. Chim. Pays–Bas, 81 (1962), 69–72.
J. Chem. Soc. (1955) 3549–3563.
Snider et al, J. Org. Chem, vol. 58, pp 3828–3839, 1993.
Fearing et al, J. Am. Chem. Soc., vol. 76, pp 4382–4385, 1954.

*Primary Examiner*—Shailendra Kumar
*Attorney, Agent, or Firm*—Keil & Weinkauf

[57] ABSTRACT

Substituted guanidine derivatives of the formula I

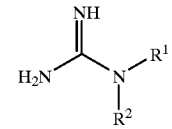

are prepared by a) converting urea into an alkylated isourea of the formula II

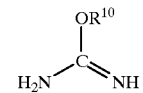

and b) reacting the alkylated isourea with a primary or secondary amine of the formula III

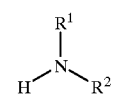

where the substituents $R^1$, $R^2$ and $R^{10}$ have the meanings explained in the description.

9 Claims, No Drawings

PREPARATION OF SUBSTITUTED GUANIDINE DERIVATIVES

The present invention relates to a process for preparing substituted guanidinium compounds by reacting urea with dialkyl sulfates to give isourea derivatives and reaction thereof with primary or secondary amines to give substituted guanidinium compounds.

Substituted guanidinium compounds are widespread in nature. Important representatives of this class of substances are, for example, amino acids such as arginine and creatine. Substituted guanidine compounds are also known as sterically hindered bases, as biocides and as complex ligands. However, the industrial applicability of most of the compounds of this type is greatly restricted owing to the high costs of their preparation.

One example of a biologically active guanidine derivative is creatine which, as "the cell's energy carrier", is employed as dietary supplement in the food and drugs sectors.

The preparation of creatine is described, for example, in EP-A-0 754 679 and the further literature quoted therein, the maximum yields obtained being only 70%.

One disadvantage of the abovementioned syntheses of guanidinium compounds is the use of aqueous solutions of pure cyanamide. These solutions are very costly and, owing to the instability of cyanamide, generally not widely available.

The synthesis of guanidinium salts starting from pure O-alkylisourea derivatives is described by R. B. Fearing and S. W. Fox in J. Am. Chem. Soc. 76 (1954) 4382–4385.

The reaction of sarcosine with O-methylisourea hydrochloride, described by E. Schütte in Hoppe-Seylers Z. Physiol. Chemie 279 (1943) 52–59, affords creatine in a yield of only 21%.

JP 077364 describes the reaction of a solution of sodium sarcosinate with O-methylisourea methyl sulfate at pH 11 to give creatine.

A feature common to the abovementioned guanidinium syntheses is the use of pure starting materials.

The preparation of O-alkylisoureas by acid-catalyzed reaction of anhydrous cyanamide with alcohols has been described (H. Krommer, Chem. Ztg. 98 (1974) 617–618; J. Stieglitz, R. H. McKee, Chem. Ber. 33 (1900) 1517–1519).

One disadvantage of this reaction is the use of anhydrous cyanamide, which is costly and not readily available.

Another possibility for preparing O-alkylisoureas is to react urea with dialkyl sulfates. Thus, JP 78-77365 describes the synthesis of O-methylisourea by alkylation of urea with dimethyl sulfate.

N. Heyboer et al. in Rec. Trav. Chim. Pays-Bas, 81 (1962), 69–72, J. W. Janus in J. Chem. Soc. (1955) 3551–3552 and D. J. Brown, E. Hoerger in J. Appl. Chem. 4 (1954), 283–284 describe the synthesis of O-alkylguanidinium salts by reacting urea with dialkyl sulfates without the use of solvents. The yields obtained in this case are distinctly below 50%.

In all the abovementioned cases, the urea and dialkyl sulfate are completely mixed and brought to a particular temperature. Because of the low solubility of urea in the reaction mixture, it dissolves continuously during the reaction, which leads to a continuous rise in temperature of the mixture and, as a rule, can be suppressed only by complicated control of the reaction.

An additional disadvantage of the abovementioned processes is the occurrence of unwanted N-alkylations and multiple alkylations, which leads to poor yields and inadequate purity of the required product from the subsequent reaction to give the guanidine compound. In addition, there is a considerable safety problem, especially with reactions on the industrial scale, because the reaction starts after a delay and is highly exothermic.

It is an object of the present invention to provide a low-cost and straightforward process for preparing substituted guanidines based on widely available starting materials which does not have the abovementioned disadvantages.

We have found that this object is achieved by a process for preparing substituted guanidine derivatives of the formula I

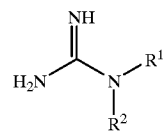

where the substituents $R^1$ and $R^2$ have the following meanings, independently of one another:

$R^1$ H, $C_1$–$C_{20}$-alkyl, $C_2$–$C_{10}$-alkenyl, $C_3$–$C_8$-cycloalkyl;

$R^2$ $C_1$–$C_{20}$-alkyl, $C_2$–$C_{10}$-alkenyl, $C_3$–$C_8$-cycloalkyl, —($C_1$–$C_{20}$-alkylene)—$COOR^3$, —($C_1$–$C_{20}$-alkylene)—$CONR^4R^5$, —($C_1$–$C_{20}$-alkylene)—CN, —($C_1$–$C_{20}$-alkylene)—$SO_2R^6$, —[$(CH_2)_m$—X—]$_p$—[$(CH_2)_n$—Y—]$_q$—[$(CH_2)_o$]$_r$—Z;

m, n, o
 0 to 10;

p, q, r
 0 to 50,000;

X O, NH;

Y N—[$(CH_2)_m$—X—]$_p$—[$(CH_2)_n$—Y—]$_q$—[$(CH_2)_o$]$_r$—Z;

Z OH, $NH_2$;

$R^3$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, $N(R^7)_4$;

$R^4$ and $R^5$ independently of one another H, $C_1$–$C_{20}$-alkyl, $C_2$–$C_{10}$-alkenyl, $C_3$–$C_8$-cycloalkyl, $C_6$–$C_{18}$-aryl;

$R^6$ $OR^8$, $N(R^9)_2$;

$R^7$ H, $C_1$–$C_{20}$-alkyl;

$R^8$ H, $C_{1-C20}$-alkyl, $C_2$–$C_{10}$-alkenyl, $C_3$–$C_8$-cycloalkyl, Na, K, Li, Ca, Mg, $N(R^7)_4$; $C_6$–$C_{18}$-aryl, Na, K, Li, Ca, Mg, $N(R^7)_4$;

$R^9$ H, $C_{1-C20}$-alkyl, $C_2$–$C_{10}$-alkenyl, $C_3$–$C_8$-cycloalkyl, $C_6$–C18-aryl, which comprises a) converting urea into an alkylated isourea of the formula II

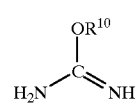

where $R^{10}$ can be $C_1$–$C_{20}$-alkyl, b) reacting the alkylated isourea II with a primary or secondary amine of the formula III

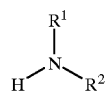

where the substituents R¹ and R² have the abovementioned meanings, to give the substituted guanidine compounds of the formula I.

The novel process satisfies in particular economic limiting conditions such as low costs of starting materials, easy industrial implementation and improved yields and adequate purity of the product.

The process is particularly distinguished by a combination of low-cost starting materials. Thus, in the first stage for preparing O-alkylisoureas there is use of urea, which is widely available at very low cost, in place of the more costly pure cyanamide, for example. In the second step of the process there is use of technical, nonpurified O-alkylisourea in place of pure O-methylisourea sulfate or O-methylisourea bisulfate or O-methylisourea hydrochloride.

It is possible by the novel process to prepare the alkylated isourea derivatives of the formula II by reacting urea with the usual alkylating agents in the literature, such as alkyl halides of the formula $C_1$–$C_{20}$-alkyl-X (X=Cl, Br, I) or, preferably, dialkyl sulfates of the formula $(R^{10}O)_2$—$SO_2$.

It is possible in this way to prepare the alkylated isourea derivatives of the first stage in the synthesis by adding dialkyl sulfate of the formula $(R^{10}O)_2$—$SO_2$ to a mixture of a) 0.01 to 1 equivalent, preferably 0.01 to 0.8 equivalent, particularly preferably 0.01 to 0.5 equivalent, based on urea, of an acid, for example organic acids such as p-toluenesulfonic acid, methylsulfonic acid, acetic acid, chloroacetic acid, trifluoroacetic acid and, preferably, mineral acids such as HCl, $H_2SO_4$, $HBF_4$ and $H_3PO_4$ and b) urea.

In the case of the mineral acids it is also possible in particular to use mixtures such as hydrochloric acid/sulfuric acid or hydrochloric acid/phosphoric acid in a ratio of from 20/1 to 5/1, in particular 15/1 to 8/1.

Compounds suitable as dialkyl sulfates are those where $R^{10}$ may be branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Particularly preferred dialkyl sulfates are those where $R^{10}$ is linear or branched aliphatic radicals having 1 to 6 carbon atoms, such as methyl, ethyl, propyl, butyl, pentyl or hexyl.

Solvents which can be employed are, inter alia, dipolar aprotic solvents or else water and alcohols, preferably methanol or ethanol. The urea concentration in this case is in the range from 10 to 99% by weight, preferably in the range from 30 to 99% by weight, particularly preferably in the range from 50 to 99% by weight.

However, it is also possible entirely to dispense with the solvent and to add only the acid, with or without addition of emulsifiers such as alkylated polyethers in small amounts.

In the alkylation with dialkyl sulfate without addition of another solvent, the resulting O-alkylisourea is present as liquid phase and thus also serves as solvent or solubilizer for subsequently added urea, so that alkylation reactions carried out thereafter where appropriate can take place in a single-phase liquid system.

The dialkyl sulfate is added to the urea in equal portions over a period of from 0.5 to 10 h, preferably from 1 to 6 h, particularly preferably from 2 to 5 h.

The molar ratio of urea to dialkyl sulfate is in the range from 1:0.5 to 1:1.5, preferably in the range from 1:0.7 to 1:1.2, particularly preferably in the range from 1:0.8 to 1:1.

The reaction is carried out at from −20 to 90° C., preferably from −10 to 80° C., in particular from 0 to 75° C.

The addition is followed as a rule by stirring for from 0.5 to 10 h, preferably 1 to 5 h.

The reaction parameters introduced in the first step of the novel process, such as addition of an acid, carrying out the alkylation at low temperatures, and a semi-batchwise procedure in which dialkyl sulfate is metered into the urea, have made it possible to increase the yield and selectivity in the alkylation of urea.

The O-alkylisourea formed in step a) can, without further purification, be reacted in a second stage of the process with primary or secondary amines to give substituted guanidine compounds.

In principle, all the claimed amines of the formula III are suitable for reaction with the isourea derivatives of the formula II. These may be either aliphatic or cycloaliphatic, primary or secondary amines, as well as amino carboxylic acids and amino sulfonic acids and their derivatives. It is also possible in the novel process to react primary and secondary amines which contain additional amino or imino groups, and amino-containing oligomers and polymers.

Alkyl radicals which may be mentioned for $R^1$ to $R^5$ and for $R^7$ to $R^9$ are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals which may be mentioned for $R^1$ to $R^5$ and for $R^8$ and $R^9$ are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Alkylene radicals which may be mentioned for $R^2$ are branched or unbranched $C_1$–$C_{20}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2- dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene or n-eicosylene.

The 1- to 20-membered alkylene chains may be substituted by the following radicals:

$C_1$–$C_6$-alkyl, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl;

mercaptomethyl, 1-aminobutyl, 1-carboxyethyl;

arylalkyl, for example benzyl, p-hydroxybenzyl, indolylmethyl.

Cycloalkyl radicals which may be mentioned for $R^1$ to $R^5$ and for $R^8$ and $R^9$ are branched or unbranched $C_3$–$C_8$-cycloalkyl radicals, preferably cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl or cyclooctyl.

The cycloalkyl radicals may be substituted by one or more, eg. 1 to 3, radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals or contain 1 to 3 heteroatoms such as sulfur, nitrogen, whose free valences can be saturated by hydrogen or $C_1$–$C_4$-alkyl, or oxygen in the ring.

Suitable alkoxy radicals for $R^6$ are those having 1 to 20 carbon atoms, preferably having 1 to 12 carbon atoms, particularly preferably 1 to 8 carbon atoms. Examples which may be mentioned are:
methoxy-
isopropoxy-
1-methylpropoxy-
n-pentoxy-
3-methylbutoxy-
2,2-dimethylpropoxy-
1-methyl-1-ethylpropoxy-
octoxy-
ethoxy-
n-propoxy-
n-butoxy-
2-methylpropoxy-
1,1-dimethylpropoxy-
hexoxy-
heptoxy-
2-ethylhexoxy- Suitable and preferred mono- or disubstituted amino radicals for $R^6$ are those containing alkyl radicals having 1 to 20, preferably 1 to 12, carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Suitable tetraalkylammonium radicals for $R^3$ and $R^8$ are those containing alkyl radicals having 1 to 20, preferably 1 to 12, particularly preferably 1 to 6, carbon atoms, such as methyl, n-propyl, isopropyl, 2-methylpropyl, 1,1-dimethylpropyl, 1-methylpropyl, 2,2-dimethylpropyl, 1-methyl-1-ethylpropyl, n-butyl, 3-methylbutyl, n-pentyl and hexyl.

Aryl means aromatic rings or ring systems having 6 to 18 carbon atoms in the ring system, for example phenyl or naphthyl, each of which may be substituted by one or more radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Amines preferably used are all primary and secondary amines which are soluble in water or in water-miscible solvents. Preferred representatives among the simple amines are, inter alia, methylamine, ethylamine, n-propylamine, 2-propylamine, butylamine, isobutylamine, aniline, benzylamine and anthranilic acid. Other amino-containing compounds which are preferably employed are, inter alia, taurine and amino carboxylic acids such as glycine, alanine, valine, proline, leucine, phenylalanine, lysine, methionine, cysteine, aspartic acid, iminodiacetic acid, sarcosine and their esters, amides and nitriles and their salts.

The very particularly preferred compound of the formula III is sarcosine which can be used both as free acid and, in particular, as Na or K salt in the form of a 5 to 60% by weight, preferably 35 to 45% by weight, aqueous solution.

It is also possible to employ in the novel process water-soluble, amino-containing oligomers and polymers such as alkylenediamines, dialkylenetriamines and so on to polyalkylenepolyamines or polyetherdiamines. Preferred representatives of this group are ethylenediamine, propylenediamine, butylenediamine, hexamethylenediamine, diethylenetriamine, triethylenetetramine, tetraethylenepentamine, pentaethylenehexamine, hexaethyleneheptamine and branched or linear polyalkylenepolyamines.

Suitable and preferred polyalkylenepolyamines are polyethyleneimines which have, for example, molecular weights of from 200 to 10 million, preferably 1000 to 3 million. Polyethyleneimines with molecular weights of from 2000 to 1,300,000 are particularly preferably employed.

The polyetherdiamines are prepared, for example, by reacting polyalkylene glycols with ammonia. The polyalkylene glycols may contain from 2 to 50, preferably 2 to 40, alkylene oxide units. Possible examples thereof are polyethylene glycols, polypropylene glycols, polybutylene glycols or else block copolymers of ethylene glycol and propylene glycol, block copolymers of ethylene glycol and butylene glycol or block copolymers of ethylene glycol, propylene glycol and butylene glycol. Suitable for preparing the polyetherdiamines apart from the block copolymers are random copolymers of ethylene oxide and propylene oxide, with or without butylene oxide. Polyetherdiamines are also derived from polytetrahydrofurans which have 2 to 75 tetrahydrofuran units. The polytetrahydrofurans are likewise converted into the corresponding $\alpha,\omega$-polyetherdiamines by reaction with ammonia. Polyethylene glycols or block copolymers of ethylene glycol and propylene glycol are preferably used for preparing the polyetherdiamines.

Other suitable amino-containing water-soluble polymers are polyvinylamines, which are obtainable by homo- and/or copolymerization of N-vinylformamide and subsequent hydrolysis of the polymers, and polymers containing vinyllamine units. Substances of this type are known, cf. EP-B-0 071 050 and EP-B-0 216 387. Suitable and preferred polymers are hydrolyzed homopolymers of N-vinylformamide having a degree of hydrolysis of from 1 to 100, preferably 80 to 100, % and partially or completely hydrolyzed copolymers of N-vinylformamide and vinyl formate or vinyl acetate. The N-vinylformamide units in the copolymers are preferably from 80 to 100% hydrolyzed. Depending on the hydrolysis conditions, the monomers such as vinyl formate or vinyl acetate in the polymer may be partially or completely hydrolyzed to vinyl alcohol units. Other comonomers suitable for preparing hydrolyzed copolymers of N-vinylformamide are monoethylenically unsaturated carboxylic acids such as acrylic acid, methacrylic acid or maleic acid, N-vinylpyrrolidone and acrylonitrile.

Other amino-containing water-soluble polymers are polyallylamines. These polymers contain at least 3 allylamine units and have molecular weights of up to 10 million.

The use of technical products in the novel process is particularly advisable when no other unwanted reactive amines are present and it is particularly economically advantageous because, for example, purification of the amine is costly and complicated.

The substituted isourea derivatives can be reacted with the abovementioned amines in water or a water-miscible solvent, or a mixture thereof. The pH normally used for this will be in the region of the pK of the amine, ie. in a pH range from 6 to 14, preferably from 8 to 12, particularly preferably from 9 to 11.5.

The molar ratio of O-alkylisourea to primary or secondary amine is in the range from 0.9 to 5.0, preferably from 1.0 to 2.0.

The reaction temperatures in the second stage are in the range from −20 to 100° C., preferably from 0 to 80° C., particularly preferably from 10 to 60° C.

The sequence of addition of the reactants for the reaction in the second stage of the process has no special significance. As a rule, the substituted isourea is added to the primary or secondary amine, which can preferably be present in aqueous or alcoholic solution.

The addition can take place over a period of from 0.5 to 10 h, preferably from 1 to 3 h.

The pH can be maintained, depending on the initial pH of the base, by employing either acids such as $CO_2$, $SO_2$, HCl, $HNO_3$, $H_2SO_4$, $H_2SO_3$, $H_3PO_3$, $H_3PO_2$ and $H_3PO_4$, and/or bases such as NaOH, KOH, LiOH, $Ca(OH)_2$, $Ba(OH)_2$, $Mg(OH)_2$. If the amines ought to be present in basic and not in neutralized or partially neutralized form, only acids are required.

Examples of preferred acids are $CO_2$, $H_2SO_4$, $H_3PO_4$. However, it is also possible and preferable to employ mixtures of these and other acids.

The required guanidinium derivatives are isolated in a manner known per se. Thus, for example, creatine can be obtained as crystals by cooling the filtered reaction solution to −20 to 60° C., in particular 0 to 40° C. After filtration, the purity can be improved where appropriate by a recrystallization. However, it is also possible to remove the product from the reaction mixture by extraction and then to isolate it pure by distillation or crystallization.

It is particularly surprising that the yields of the novel reaction based on the content of cyanamide (1st stage) and O-alkylisourea (2nd stage) are comparable on use of the technical starting materials with those on reaction of pure cyanamide and O-alkylisoureas. When the purification step for the respective preparation of pure cyanamide and O-alkylisourea is taken into account, the yield is far higher because of the smaller number of process steps.

In addition, it is possible to achieve even higher conversions if the low-cost isourea compound is employed in excess relative to the amine in the second step of the process, which is frequently uneconomical on use of pure O-alkylisourea. The purity of the isolated guanidinium salt is comparable with that prepared from pure O-alkylisourea. This is attributable in particular to the high purity of the isourea derivatives obtained according to the invention.

The following example explains the process for preparing substituted guanidinium derivatives in detail.

EXAMPLE 1

Preparation of Creatine

Stage 1:

Synthesis of technical O-methylisourea 66 g of urea were mixed with 2 ml of dry methanol and 2 ml of methanesulfonic acid in a 250 ml three-neck flask with mechanical stirrer, heating bath, reflux condenser and drying tube, and then heated to 40° C. Immediately after the temperature was reached, 1 mol of dimethyl sulfate was metered in at a rate of 126 g per h by a metering pump. During the metering in, the reaction mixture started to warm up and was kept at 70° C. by cooling in ice. After the metering in was complete, stirring was continued at 70° C. for 2 h. Cooling resulted in 196 g of a colorless mobile oil which, according to HPLC, contained 92% O-methylisourea methyl sulfate, corresponding to a yield of 97%.

The content of N-methyl-O-methylisourea methyl sulfate was 0.51%, corresponding to a yield of 0.5%, and the urea content was 5.2%.

Stage 2:

Reaction of sarcosine sodium salt solution with technical O-methylisourea at pH 11

A total of 16.2 g of 50% strength sulfuric acid was added to a mixture of 138 g of 40.1% strength aqueous sodium sarcosinate solution and 53 g of water to adjust to pH 11.0 in a 2 l reactor with reflux condenser, paddle stirrer, thermostat and pH-controlled metering of sulfuric acid and sodium hydroxide solution. Then 146 g of the 92% strength methanolic O-methylisourea methyl sulfate from stage 1 were metered in continuously at 20° C. over a period of 2 h by means of a balance-controlled metering pump. The pH was kept at 11.0 during this by adding 143 g of 25% strength aqueous sodium hydroxide solution. Creatine started to precipitate even during the metering in. After the addition was complete, stirring was continued at 20° C. for 6 h. No alkylating potential (Preußmann test) was detectable after this period. The mixture was then cooled at 0 to 5° C. for 2 h. The colorless crystals which had formed were filtered off, washed with 2×50 ml of water and then dried at 60° C. under reduced pressure to result in 63.3 g of crystals with a creatine content of 88% and a residual water content of 12%, corresponding to an isolated yield of 85%.

The creatine content in the mother liquor was 1.1%, and thus the calculated yield of the reaction was 94%.

EXAMPLE 2

Preparation of Creatine

Stage 1:

Synthesis of technical O-methylisourea 66 g of urea were mixed with 2 ml of 50% strength aqueous sulfuric acid in a 250 ml three-neck flask with mechanical stirrer, heating bath, reflux condenser and drying tube, and then heated to 40° C. Immediately after the temperature was reached, 1 mol of dimethyl sulfate was metered in at a rate of 126 g per h by a metering pump. During the metering in, the reaction mixture started to warm up and was kept at max. 70° C. by cooling in ice. After the metering in was complete, stirring was continued at 70° C. for 2 h. Cooling resulted in 194 g of a colorless mobile oil which, according to HPLC, contained 90% O-methylisourea methyl sulfate, corresponding to a yield of 94%.

The content of N-methyl-O-methylisourea methyl sulfate was 0.47%, corresponding to a yield of 0.5%, and the urea content was 5.7%.

Stage 2:

Reaction of sarcosine sodium salt solution with technical O-methylisourea

A total of 17.2 g of 37% strength hydrochloric acid was added to a mixture of 138 g of 40.1% strength aqueous sodium sarcosinate solution to adjust to pH 11.0 in a 2 l reactor with reflux condenser, paddle stirrer, thermostat and pH-controlled metering of sulfuric acid and sodium hydroxide solution. Then 149 g of the 90% strength O-methylisourea methyl sulfate from stage 1 were metered in continuously at 20° C. over a period of 2 h by means of a balance-controlled metering pump. The pH was kept at 11.0 during this by adding 137 g of 25% strength aqueous sodium hydroxide solution. Creatine started to precipitate even during the metering in. After the addition was complete, stirring was continued at 20° C. for 6 h. No alkylating potential (Preußmann test) was detectable after this period. The mixture was then cooled at 0 to 5° C. for 2 h. The colorless crystals which had formed were filtered off, washed with 2×50 ml of ice-water and then dried at 60° C. under reduced pressure to result in 65.7 g of crystals with a creatine content of 87% and a residual water content of 12%, corresponding to an isolated yield of 87%.

The creatine content in the mother liquor was 0.8%, and thus the calculated yield of the reaction was 93%.

EXAMPLE 3

Preparation of Creatine

Stage 1:

Synthesis of technical O-methylisourea 60 g of urea were added in portions to a mixture of 126 g of dimethyl sulfate and 1 g of 50% strength aqueous sulfuric acid at 70° C. in a 250 ml three-neck flask with mechanical stirrer, heating bath, reflux condenser and drying tube in such a way that the temperature could be kept constant. After 30 min, all the urea had dissolved, and the mixture was then stirred at 70° C. for 1 h. It was then cooled to 60° C., and a further 60 g of urea were dissolved in the reaction mixture. 1 mol of dimethyl sulfate was metered in to the solution at a rate of 126 g per h by a metering pump, the mixture being homogeneous throughout the addition and the temperature being kept at 60° C. After the metering in was complete, a further 60 g of urea were added and, after it had dissolved, the metering in of dimethyl sulfate was repeated. The procedure was then repeated, ie. further urea and dimethyl sulfate were added in the manner described.

Cooling of the clear reaction mixture resulted in 726 g of a colorless mobile oil which, according to HPLC, contained 97% O-methylisourea methyl sulfate, corresponding to a yield of 95%.

The content of N-methyl-O-methylisourea methyl sulfate was 0.32%, corresponding to a yield of 0.3%, and the urea content was 0.5%.

Stage 2:

Reaction of sarcosine sodium salt solution with technical O-methylisourea

A total of 17.2 g of 37% strength hydrochloric acid was added to a mixture of 138 g of 40.1% strength aqueous sodium sarcosinate solution to adjust to pH 11.0 in a 2 l reactor with reflux condenser, paddle stirrer, thermostat and pH-controlled metering of sulfuric acid and sodium hydroxide solution. Then 120 g of the 97% strength O-methylisourea methyl sulfate from stage 1 were metered in continuously at 40° C. over a period of 2 h by means of a balance-controlled metering pump. The pH was kept at 11.0 during this by adding 134 g of 25% strength aqueous sodium hydroxide solution. Creatine started to precipitate even during the metering in. After the addition was complete, stirring was continued at 40° C. for 2 h. No alkylating potential (Preußmann test) was detectable after this period. The mixture was then cooled at 0 to 5° C. for 2 h. The colorless crystals which had formed were filtered off, washed with 2×50 ml of ice-water and then dried at 60° C. under reduced pressure to result in 69.3 g of crystals with a creatine content of 89% and a residual water content of 11%, corresponding to an isolated yield of 94%.

The creatine content in the mother liquor was 0.4%, and thus the calculated yield of the reaction was 97%.

What is claimed is:

1. A process for preparing creatine which comprises
   a) converting urea into an alkylated isourea of the formula II

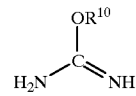

where $R^{10}$ can be $C_1$–$C_{20}$-alkyl and
   b) reacting the alkylated isourea II with sarcosine to give creatine, wherein the alkylated isourea prepared in step a) is employed immediately, without isolation, in step b).

2. The process of claim 1, wherein in step a) urea is reacted with dialkyl sulfate of the formula $(R^{10}O)_2$—$SO_2$.

3. The process of claim 2, wherein in step a) an acidified urea solution or an acidified urea suspension is reacted at from −20 to 90° C. with dialkyl sulfate of the formula $(R^{10}O)_n$—$SO_2$.

4. The process of claim 2, wherein in step a) the reaction of urea with dialkyl sulfate of the formula $(R^{10}O)_n$—$SO_2$ is carried out at from −20 to 90° C. without solvent.

5. The process of claim 2, wherein in step a) the dialkyl sulfate is metered into the urea.

6. The process of claim 1, wherein the sarcosine reacted in step b) is a Na or K salt.

7. The process of claim 3, wherein in step a) the reaction of urea with dialkyl sulfate of the formula $(R^{10}O)_n$—$SO_2$ is carried out at from −20 to 90° C. without solvent.

8. The process of claim 3, wherein in step a) the dialkyl sulfate is metered into the urea.

9. The process of claim 3, wherein in step a) the reaction of urea with dialkyl sulfate of the formula $(R^{10}O)_n$—$SO_2$ is carried out at from −20 to 90° C. without solvent.

* * * * *

UNITED STATES PATENT AND TRADEMARK OFFICE
CERTIFICATE OF CORRECTION

PATENT NO.: 6,093,848

DATED: July 25, 2000

INVENTOR(S): GREINDL et al.

It is certified that error appears in the above-identified patent and that said Letters Patent is hereby corrected as shown below:

Col. 10, claim 9, line 59, "claim 3" should be --claim 4--.

Signed and Sealed this

Seventeenth Day of April, 2001

Attest:

NICHOLAS P. GODICI

Attesting Officer

Acting Director of the United States Patent and Trademark Office